United States Patent [19]
Takeda et al.

[11] Patent Number: 5,332,660
[45] Date of Patent: Jul. 26, 1994

[54] **GENE ENCODING ASPARTIC ACID SECRETORY PROTEINASE OF *CANDIDA ALBICANS* AND A METHOD OF USING THE GENE FOR THE DETECTION OF *CANDIDA ALBICANS***

[75] Inventors: Osamu Takeda, Otsu; Hiroyuki Mukai, Moriyama; Kiyozo Asada, Otsu; Hideyo Yamaguchi, Kawasaki; Ikunoshin Kato, Uji, all of Japan

[73] Assignee: Takara Shuzo Co., Ltd., Japan

[21] Appl. No.: 32,393

[22] Filed: Mar. 15, 1993

Related U.S. Application Data

[63] Continuation of Ser. No. 729,414, Jul. 12, 1991, abandoned.

[30] Foreign Application Priority Data

Jul. 26, 1990 [JP] Japan .................. 2-196226
Apr. 22, 1991 [JP] Japan .................. 3-116596

[51] Int. Cl.$^5$ .............................................. C12N 15/52
[52] U.S. Cl. ........................................ 435/6; 435/91.2; 536/23.74; 536/23.2
[58] Field of Search .............. 536/23.74, 23.7, 24.33, 536/24.32, 23.2; 435/91, 6, 91.2

[56] References Cited

U.S. PATENT DOCUMENTS 4,683,202  7/1987  Mullis .................................. 435/91

OTHER PUBLICATIONS

Cutler, J. E. et al. (1988) Journal of Clinical Microbiology vol. 26 (9), pp. 1720–1724.

Maniatis et al. (1982) Molecular Cloning: A Laboratory Manual. Cold Spring Harbor, N.Y. pp. 280–311 and 187–197.

"Comparative production and rapid purification of Candida acid proteinase from protein-supplemented cultures", Infection And Immunity, vol. 58, No. 2, Feb. 1990, pp. 508–514, Ray et al.

"Production and characterization of monoclonal antibodies against secretory proteinase of *Candida albicans* CBS 2730", Zentralblatt fur Bakteriologie Mikrobiologie und Hygiene, vol. 268, No. 1, 1988, pp. 62–73, Borg. M. et al.

"Molecular Cloning", J. Sambrook et al., 1989, Cold Spring Harbor Laboratory Press, p. 8.2.

"Evidence for a role for secreted aspartate proteinase of *Candida albicans* in vulvovaginal candidiasis", The Journal of Infectious Diseases, vol. 161, No. 6, Jun. 1990, pp. 1276–1283, De Bernardis, F. et al.

"Exponential amplification of nucleic acids: new diagnostics using DNA polymerases and RNA replicases", Trends in Biotechnology, vol. 9, No. 2, Feb. 1991, pp. 53–58, Lizardi, P. M. et al.

Snyder et al. (1987) Methods in Enzymology, vol. 154, "ygt11: Gene Isolation w/Antibody Probes and Other Applications", pp. 107–128.

Tongi et al. (Jul. 1991) FEBS Lett., vol. 286 (1,2), "Isolation & Nucleotide Sequence of the Extracellular Acid Protease Gene (ACP) from the Yeast *Candida tropicalis*", pp. 181–185.

Ganesan et al. (Sep. 1991) Infection & Immunity, vol. 59, "Molecular Cloning of the Secretory Acid Proteinase Gene from *Candida albicans* and Its Use as a Species-Specific Probe" pp. 2972–2977.

*Primary Examiner*—Margaret Parr
*Assistant Examiner*—Lisa Arthur
*Attorney, Agent, or Firm*—Wenderoth, Lind & Ponack

[57] ABSTRACT

This invention is directed to a gene sequence for secretory aspartic proteinase (SEQ ID No. 1) which is specific to pathogenic Candida yeast, to a highly sensitive method for detection of said gene in a sample solution and a kit used therefor.

2 Claims, No Drawings

GENE ENCODING ASPARTIC ACID SECRETORY PROTEINASE OF *CANDIDA ALBICANS* AND A METHOD OF USING THE GENE FOR THE DETECTION OF *CANDIDA ALBICANS*

This application is a continuation of now abandoned application, Ser. No. 07/729,414, filed on Jul. 12, 1991.

The present invention relates to a gene of a yeast belonging to the genus Candida and a method for detection thereof. More particularly, the present invention relates to a secretory aspartic proteinase gene of a yeast belonging to the genus Candida and detection thereof. The present invention also relates to a detection kit for detecting the same.

PRIOR ART

Irrespective of its significant clinical meaning, any effective method for diagnosis closely related to treatment has not been established for candidiasis, one of the serious diseases in opportunistic infections, which tends to be increasing in recent years because of highly intensive medical treatment. A reagent for diagnosis currently commercially available is the one for determining anti-Candida mannan antibody in serum using mannan antigen which is one of the cell wall components of pathogenic Candida yeast. However, this reagent for diagnosis often shows a significantly high level also in healthy individuals (Koji Takagi, Nobuyuki Shimono, Toshiyuki Ishimaru, Kaoru Okada, Yoshiro Sawae: Summary of a 10th lecture at a medical mycology symposium, page 13.

There are also methods for biochemically assaying metabolites of Candida or component of the Candida cells. However, these methods also sometimes provide a significantly high level even in patients who do not suffer pathogenically from Candidiasis. It has thus been desired to establish a method for diagnosis specific to Candidiasis.

Problems to be solved by the invention:

On the other hand, a variety of genetic diagnoses have been developed in recent years. Characteristics of pathogenic Candida yeast are determined by its gene and if the DNA sequence characteristic of the pathogenic Candida yeast is determined, it would be possible to determine its presence.

Turning to yeasts belonging to the genus Candida, a strain capable of producing secretory aspartic proteinase is limited to a pathogenic yeast and if the DNA sequence of secretory aspartic proteinase characteristic of the pathogenic yeast is rapidly determined with high sensitivity, it would be possible to determine the presence of pathogenic Candida yeast in a simple manner.

That is, an object of the present invention is to reveal a DNA sequence of secretory aspartic proteinase specific to pathogenic Candida yeast and to provide a method for detection thereof and a kit used therefor.

Means to solve the problems:

In summary, the present invention relates to a secretory aspartic proteinase gene of a yeast belonging to the genus Candida which is represented by SEQ ID No. 1 of the Sequence Listing. The present invention also relates to a method for detection of a yeast belonging to the genus Candida which comprises detecting the gene described above. The present invention further relates to a detection kit used for the method for detection described above comprising a specific primer for amplifying a secretory aspartic proteinase gene of a yeast belonging to the genus Candida and a probe for detecting the amplified DNA.

The whole sequence of nucleic acids of the secretory aspartic proteinase gene of pathogenic *Candida albicans* can be determined, for example, by the following procedures.

(1) As a pathogenic Candida yeast, for example, pathogenic *Candida albicans* No. 114 strain is cultivated and mRNA is prepared from the cultured Candida yeast.

(2) Using M13 M4-oligo(dT) primer for synthesis of cDNA shown by SEQ ID No. 2 of the Sequence Listing, cDNA is synthesized from mRNA.

(3) N-terminal amino acid sequence of secretory aspartic proteinase of pathogenic *Candida albicans* No. 114 has already been determined as shown in SEQ ID No. 3 of Sequence Listing. Based on the amino acid sequence, a mix primer for PCR [Polymerase Chain Reaction: Saiki et al., Science, 230, 1350–1354 (1985)] for cloning of the proteinase gene and a mix probe for detection are synthesized and purified. Using the mix primers and a random primer, a gene coding for the N-terminal portion of the proteinase is amplified and cloned according to the method described in Japanese Patent Application No. 2-29549 to determine its nucleic acid sequence.

(4) Based on the nucleic acid sequence determined in the foregoing step, a nested PCR primer and a probe for detection are synthesized and purified. According to the PCR using the primer and M13 M4 primer (Takara Shuzo), a gene containing the C-terminal portion of the proteinase is amplified and cloned to determine its nucleic acid sequence.

(5) Based on the nucleic acid sequence determined at the foregoing step, a nested PCR primer is synthesized and purified. After blunting the cDNA by T4 DNA polymerase, EcoRI adaprase is ligated with the cDNA and then ligated with phage vector λgt10 digested with EcoRI to prepare template DNA. Next, by PCR using the nested PCR primer and λgt10 reverse primer, a gene containing the N-terminal portion of the proteinase is amplified and cloned to determine its nucleic acid sequence.

(6) SEQ ID No. 4 of the Sequence Listing is nucleic acid sequence of 327 bp coding for the N-terminal portion of the proteinase, SEQ ID No. 5 of the Sequence Listing is nucleic acid sequence of 933 bp coding for the C-terminal portion of the proteinase and SEQ ID No. 6 of the Sequence Listing is nucleic acid sequence of 547 bp coding for the N-terminal portion of the proteinase. The nucleic acid sequence of the secretory aspartic proteinase gene shown by SEQ ID No. 1 of the Sequence Listing is determined from these nucleic acid sequences. SEQ ID No. 7 of the Sequence Listing indicates the full length of cDNA and the amino acid sequence of the proteinase.

Within this gene, a specific region to pathogenic Candida yeast is included. By detecting this region, the presence of the yeast can be determined.

For the detection, a method for genetic detection such as Southern hybridization, etc. may be used but PCR method is the one for detection of a gene with the highest sensitivity for now. For amplifying a selected region by the PCR method, a pair of oligonucleotide primer DNAs are required. In order to increase detection sensitivity, a pair of primer DNAs are additionally required. These primers may be those which can be annealed to the determined region described above.

Examples of such primers are Primer 1 shown by SEQ ID No. 8, Primer 2 shown by SEQ ID No. 9, Primer 3 shown by SEQ.ID No. 10, Primer 4 shown by SEQ ID No. 11, Primer 5 shown by SEQ ID No. 12, etc., of the Sequence Listing. These primers may be synthesized with a DNA synthesizer and purified by HPLC.

The pathogenic Candida yeast to be detected may be prepared by a sample such as serum, etc., infected with pathogenic Candida.

Turning to the PCR method, a kit for amplifying gene containing Taq-polymerase and an apparatus for automated gene amplification are commercially available from Takara Shuzo Co., Ltd. Using the same in combination with a pair of primers of the present invention, DNA of the pathogenic Candida yeast can be amplified.

According to the PCR method, only the desired gene can be exponentially amplified by repeating an optional number of times the temperature cycle comprising a step of denaturation of DNA (94° C.), a step of annealing of primer DNA (55° C.), and a step of enzymatic synthesis of complementary DNA strand (72° C.), using as the enzyme, e.g., heat-resistant Taq-polymerase.

By repeating the temperature cycle, for example, 25 times, the desired DNA is amplified to about 100,000-fold. For detecting DNA from a trace amount of a sample solution with high sensitivity, the PCR method is the most effective.

After amplification, the DNA of the secretory aspartic proteinase gene may be detected, for example, by agarose gel electrophoresis, polyacrylamide gel electrophoresis, spotting, and Southern blotting. When using spotting or Southern blotting, a probe DNA may be chosen within the amplified region. As an example, there is Probe 1 shown by SEQ ID No. 13 of Sequence Listing.

The probe DNA can be synthesized and purified in a manner similar to the primer DNA described above. The probe DNA can be labeled thereby to enable to detection with high sensitivity.

Labeling is not limited to radioactive labeling but may be any of the known labeling techniques, such as enzyme-labeling, fluorescent-labeling, biotin labeling, avidin labeling, sulfonylation labeling (chemiprobe), etc.

Using the actually selected primers, the PCR reaction of the secretory aspartic proteinase gene of pathogenic Candida yeast can be performed. Detection can be made with high sensitivity by electrophoresis, Southern hybridization, etc.

The gene region specific to the secretory aspartic proteinase of pathogenic Candida yeast is thus revealed and by detecting the region, the yeast belonging to the genus Candida can be detected with high sensitivity.

In the case of PCR, detection can be performed with high sensitivity and the pathogenic Candida yeast can be detected at an early stage so that it is possible to utilize the system for the treatment.

By assembling a pair of primers for amplifying the DNA region of the secretory aspartic proteinase of pathogenic Candida yeast and a probe for detecting the amplified DNA region in accordance with the present invention to prepare a kit, detection of the pathogenic Candida yeast can be done in a simple manner. The reagents used for the kit may be in the form of solution or in the lyophilized form.

The highly sensitive method for detection of pathogenic Candida yeast using the PCR method has been described in detail but the present invention is not limited to the PCR method. Methods for detecting a specific nucleic acid and its complementary strand with high sensitivity are all included in the present invention. An example of the other methods is a method using the Qβ-replicase amplification system [Bio/technology, 6, 1197 (1988)].

According to the present invention, the whole amino acid sequence of the secretory aspartic proteinase of pathogenic Candida yeast has been determined. Using the gene of the present invention, the proteinase can be prepared by means of genetic engineering. Polypeptides expressed by genetic engineering, polypeptides synthesized from the amino acid sequence, etc. are useful in the fields of protein engineering, immunological engineering, reagents for diagnosis, etc. Examples Hereafter the present invention is described in detail with reference to the examples but is not deemed to be limited thereto.

EXAMPLE 1

Cloning of secretory aspartic proteinase cDNA of *Candida albicans* No. 114 by PCR and determination of nucleic acid sequence (1) Preparation of mRNA of *Candida albicans* No. 114

Cultivation of *Candida albicans*, preparation of spheroplast, preparation of the whole RNA and fractionation of poly(A)-mRNA were performed in accordance with the procedures of Abe et al. ["Gene, protein—experimental procedures for blotting" (first edition) edited by Yoshiyuki Kuchino and 2 others, published Nov. 10, 1987, Soft Science Co., Ltd.]. Finally about 150 µg of mRNA was obtained from 400 ml of the culture broth.

(2) Synthesis of cDNA

Using cDNA synthesis kit of Amersham (code No. RPN. 1256) and M13 M4-oligo(dT) primer, cDNA was synthesized from about 11 µg of the poly(A)-mRNA described above to give about 2 µg of double-stranded cDNA.

(3) Cloning of the cDNA portion of the secretory aspartic proteinase by PCR

About 0.1 µg of cDNA described above was taken in a tube of 0.5 ml and 5 µl of 10-fold concentrated buffer solution for amplification [100 mM Tris-HCl, pH 8.3, 500 mM KCl, 15 mM MgCl$_2$, 0.01% (w/v) gelatin] in Gene Amp ® Kit (Takara Shuzo), 8 µl of 1.25 mM dNTP mixture (dATP, dGTP, dCTP, TTP), 0.5 µg of Mix Primer 1 shown by SEQ ID No. 14 of the Sequence Listing, 0.2 µg of random primer (alecareer) and 0.5 µl of 5 units/µl of Ampli Taq ® were added and sterilized water was further added thereto. After 50 µl of mineral oil (Sigma Co.) was overlaid, amplification was performed using an automated gene amplifier, thermal cycler (Takara Shuzo Co., Ltd.).

The reaction was carried out by repeating 35 cycles, one cycle being under the following conditions: (1) at 94° C. for 30 seconds (thermal denaturation)→(2) at 55° C. for 2 minutes (annealing)→and (3) at 72° C. for a minute (synthesis reaction).

Next, 1 µl of the reaction solution described above was taken in a tube of 0.5 ml and 5 µl of 10-fold concentrated buffer solution for amplification in Gene Amp ® Kit, 8 µl of 1.25 mM dNTP mixture, 0.5 µg of Mix Primer 2 shown by SEQ ID No. 15 of the Sequence Listing, 0.2 μg of random primer (decamer) and 0.5 μl of 5 units/μl of Ampli Taq ® were added and sterilized water was further added thereto. After 50 μl of mineral oil was overlaid, amplification was performed using an automated gene amplifier, thermal cycler.

After completion of the reaction, 10 μl of the reaction solution was taken and subjected to agarose gel (Takara Shuzo) electrophoresis and then to Southern hybridization using a nylon membrane, Hybond-N (Amersham Co.). As a probe, Mix Probe 1 shown by SEQ ID No. 16 of the Sequence Listing, the terminal of which had been labeled with [λ-$^{32}$P] ATP, was used.

As the result of the Southern hybridization, it was confirmed that a part of secretory aspartic proteinase cDNA, i.e., the fragment of about 300 bp, was amplified. The fragment was cut out of the gel and purified and then subjected to blunting using DNA blunting kit (Takara Shuzo). The fragment was subcloned to the HincII site of pUC18 vector. Using the mix probe described above as a probe, a positive clone was obtained by colony hybridization and subjected to sequencing by the dideoxy method, whereby a nucleic acid sequence of a part of secretory aspartic proteinase cDNA in *Candida albicans* No. 114, i.e., 327 bp shown by SEQ ID No. 4 of the Sequence Listing, was determined.

(4) Cloning of cDNA in the C-terminal region of secretory aspartic proteinase by nested PCR method Based on the nucleic acid sequence determined in 1-(3), Primer 1 for PCR primer and Primer 2 were synthesized and purified followed by the PCR using cDNA described in Example 1-(2) as a template. The compositions of the reaction solutions and reaction procedures were all the same as described in Example 1-(3). For the first PCR, Primer 1 and M13 primer M4 (Takara Shuzo) were used and for the second PCR, Primer 2 and M13 primer M4 were used.

As the result, it was confirmed that the fragment of about 900 bp in the C-terminal region of secretory aspartic proteinase cDNA was amplified. The fragment was subjected to subcloning and sequencing according to the procedures of Example 1-(3) to determine the nucleic acid sequence of 933 bp containing the C-terminal region of secretory aspartic proteinase cDNA of *Candida albicans* No. 114 and shown by SEQ ID No. 5 of the Sequence Listing.

(5) Cloning of cDNA in the N-terminal region of secretory aspartic proteinase by nested PCR Based on the nucleic acid sequence determined in 1-(4), Primer 3 and Primer 4 for PCR were synthesized and purified and then used as primers for PCR. As a template, the ligation product obtained by digesting cDNA described in Example 1-(2) and phage vector λgt10 with restriction enzyme EcoRI and then ligating the digestion product using cDNA cloning system λgt10 (Amersham) was used.

The composition of the reaction solution and reaction procedures for PCR were all in accordance with Example 1-(3), provided that Primer 3 and λgt10 primer reverse (Takara Shuzo) were used for the first PCR and Primer 4 and λgt10 primer reverse were used for the second PCR.

As the result, it was confirmed that the fragment of about 550 bp in the N-terminal region of secretory aspartic proteinase cDNA was amplified. The fragment was subjected to subcloning and sequencing according to the procedures of Example 1-(3) to determine the nucleic acid sequence of 547 bp containing the N-terminal region of secretory aspartic proteinase cDNA of *Candida albicans* No. 114 and shown by SEQ ID No. 6 of the Sequence Listing, and the nucleic acid the sequence and amino acid sequence of the secretory aspartic proteinase gene shown by SEQ ID Nos. 1 and 7, respectively, of the Sequence Listing were determined.

EXAMPLE 2

Detection of the DNA of secretory aspartic proteinase gene of *Candida albicans* No. 114 by PCR (1) Synthesis and purification of primer DNA and probe DNA Primer DNA and probe DNA shown by SEQ ID Nos. 8 to 13 of the Sequence Listing were synthesized using a DNA synthesizer of Applied Biosystems. After deprotection, the primer and probe were purified by ion exchange HPLC (TSK gel, DEAE-2SW column) and desalted with SEP-PAC $C_{18}$ (Waters) to give about 50 μg of each DNA.

(2) Preparation of genome DNA of *Candida albicans* No. 114

Cultivation of *Candida albicans* (60 ml), preparation of spheroplast and preparation of genome DNA were performed in accordance with the procedures of Abe et al. ["Gene, protein—experimental procedures for blotting" supra, published by Soft Science Co., Ltd.]. Finally about 340 μg of genome DNA was obtained from 60 ml of the culture broth.

(3) Amplification of the region specific to DNA of the secretory aspartic proteinase gene of *Candida albicans* No. 114 by the PCR In a tube of 0.5 ml, were taken, respectively, 680 ng of DNA of *Candida albicans* No. 114 prepared in Example 2-(2), 240 ng of mouse DNA prepared in a conventional manner, 300 ng of DNA of *Escherichia coli* HB101, 500 ng of DNA of *Saccharomyces cerevisiae*, 1 μg of human DNA and 300 ng of carp DNA. Then, 10 μl of 10 ×buffer for amplification, 16 μl of 1.25 mM dNTP mixture (dATP, dGTP, dCTP, TTP), 1 μl of 0.1 μg/μl of Primer 1, 1 μl of 0.1 μg/μl of Primer 5 and 0.5 μl of 5 units/μl of Taq-polymerase were added and 100 μl of sterilized water was further added to make the whole volume of the solution 100 μl.

After 100 μl of mineral oil was added to the upper layer, the reaction solution was subjected to amplification reaction using an automated gene amplifier, thermal cycler. The synthesis reaction was carried out by repeating 30 cycles, one cycle being under the following conditions: denaturation at 94° C. for 30 seconds→annealing at 55° C. for 2 minutes→synthesis at 72° C. for a minute.

After completion of the reaction, 10 μl of the reaction solution was taken and subjected to 1% agarose gel (Takara Shuzo) electrophoresis. The DNA was stained with ethidium bromide, whereby the amplified DNA was confirmed.

As the result, a band of 312 bp was confirmed only when *Candida albicans* No. 114 was used as a template. No amplification was noted from other DNAs.

(4) Detection of *Candida albicans* DNA by Southern hybridization

The PCR reaction solution described in Example 2-(3) was subjected to 1% agarose gel electrophoresis. After the agarose gel was denatured with an alkali, the gel was analyzed by Southern blotting on a nylon membrane (Hybond-N of Amersham) overnight. By exposing it to a UV transilluminater (254 nm) for 10 minutes, DNA was fixed on the membrane.

The membrane was subjected to prehybridization at 37° C. for 2 hours in 5 ml of a prehybridization buffer (5 ×Denhardt's, 5×SSC, 0.1% SDS, 100 μg/ml salmon sperm DNA). Next, Probe 1 labeled with $^{32}$P at the 5' end was added thereto followed by hybridization at 37° C. overnight.

The $^{32}$P labeling of the probe was performed as follows, using MEGALABEL Kit (Takara Shuzo). Sterilized water was added to a reaction solution containing 10 pmole of the probe, 1 μl of 10×phosphate buffer, 50 μCi of [μ-$^{32}$P] ATP (Amersham) and 10 units of T4-polynucleotide kinase to make the volume 10 μl and the mixture was reacted at 37° C. for 30 minutes. After the reaction, the reaction solution was treated at 94° C. for 5 minutes. The whole volume (about $10^8$ cpm) of the reaction solution was used for hybridization.

After the hybridization, the membrane was washed once with washing liquid containing 2×SSC and 0.1% SDS at room temperature for 5 minutes and then once with washing liquid containing 0.5×SSC and 0.1% SDS at 37° C. for 30 minutes.

After drying, the membrane was exposed to light in a cassette with an X ray film (Fuji Photo Film) at −70° C. for an hour to prepare an autoradiography.

As the result, the DNA of *Candida albicans* amplified by PCR was hybridized with Probe 1 and a band appeared but with other samples, no band was observed. The results indicate that DNA of *Candida albicans* was specifically amplified by Primer 1 and Primer 5 and DNA of *Candida albicans* can be specifically detected by hybridization with Probe 1.

EXAMPLE 3

Detection of DNA of secretory aspartic proteinase gene of each *Candida albicans* strain (1) Preparation of genome DNA Each colony of *Candida albicans* TIMM0167, TIMM2141, TIMM2290, TIMM2297, TIMM2325, TIMM2329 (Teikyo University Research Center for Medical Mycology) and No. 114 was scraped off and suspended in 100 μl of lysis buffer (100 mM Tris-hydrochloride, pH 7.5, 0.5% SDS, 30 mM EDTA) charged in a tube of 5 ml volume. After heat-treatment at 100° C. for 15 minutes, 50 μl of 5M potassium acetate was added. After stirring, incubation was performed at 0° C. for an hour. After centrifugation at room temperature for 5 minutes, 70 μl of the supernatant was transferred to a fresh tube of 1.5 ml volume and 70 μl of isopropyl alcohol was added thereto followed by stirring. Next, centrifugation was performed at 4° C. for 5 minutes. After the supernatant was removed, the residue was rinsed with 50 μl of 95% ethanol. After air-drying, the product was dissolved in 100 μl of sterilized distilled water.

(2) Detection of secretory aspartic proteinase gene by PCR using Primer 1 and Primer 5

After 5 μl of the DNA solution described above was taken in a tube of 0.5 ml volume, 5 μl of 10-fold concentrated buffer for amplification in Gene Amp ® Kit, 8 μl of 1.25 mM dNTP solution mixture, 0.05 μg of Primer 1, 0.05 μg of Primer 5 and 0.25 μl of 5 units/μl Ampli Taq ® were added to the DNA solution and sterilized water was further added thereto. After 50 μl of mineral oil was overlaid, amplification was performed with a thermal cycler. The reaction conditions were: 25 cycles, each cycle comprising treatments at 94° C. for 30 seconds, at 55° C. for a minute and at 72° C. for 30 seconds. After completion of the reaction, 10 μl of the reaction solution was taken and subjected to electrophoresis on agarose gel containing ethidium bromide to confirm amplification. As the result, amplification of 312 bp was noted in all of the 7 strains.

EXAMPLE 4

Examination of detection sensitivity of *Candida albicans* using nested PCR (1) Examination of concentration limit of template DNA Genome DNA of *Candida albicans* No. 114 prepared in Example 2-(2) was sequentially diluted to 10-fold with 1 ng/μl of λ-Hind III digest (Takara Shuzo) to prepare 10 ng/μl to 1 fg/μl of model template DNA.

Using 1 μl of this template DNA solution, PCR by the procedures shown in Example 3-(2) and electrophoresis subsequent thereto were performed, but Primers 1 and 3 were used as the primers. As the result, a band of 366 bp was confirmed up to 1 pg of the template DNA.

Next, 1 μl of the reaction solution after the first PCR was taken in a tube of 0.5 ml and the second PCR was carried out according to the procedures shown in Example 3-(2), but Primers 2 and 4 were used as the primers. As the result of electrophoresis, a band of 125 bp was confirmed up to 10 fg of the template DNA.

A mass of the yeast per haploid was about 20 fg. Therefore, it is theoretically detectable if at least one *Candida albicans* is present.

(2) Detection limit of *Candida albicans*

After *Candida albicans* No. 114 was cultivated by the procedures described in Example 2-(2), the yeast cell count was counted by an erythrocytometer ($1 \times 10^7$ cells/ml).

Next, the culture broth described above which showed the yeast cell count corresponding to $1 \times 10^5$, $1 \times 10^4$, $1 \times 10^3$, 100, 10 and 1 were taken, respectively, in a tube of 5 ml to prepare DNA according to the procedures described in Example 3-(1). Using 10 μl of this template solution, nested PCR was performed according to the procedures shown in Example 4-(1).

As the result, a band of 125 bp was confirmed even with the amount of DNA prepared from the yeast cell count corresponding to one. The results well coincided with those in Example 4-(1).

EXAMPLE 5

Preparation of kit for amplification/detection of pathogenic Candida yeast

As primers for amplification of DNA, Primers 1 and 3 were dissolved in 20 μl of TE buffer to have 20 μM solution, respectively, thereby to prepare Candida Primer A-1 solution (A-1 agent). In a similar manner, Primers 2 and 4 were dissolved in 20 μl of TE buffer to have 20 μM solution, respectively, thereby to prepare Candida Primer A-2 solution (A-2 agent). As the probe for detection of DNA, 1 μg of Probe 1 was dissolved in 20 μl of TE buffer to prepare Candida Probe B-1 solution (B-1 agent). A-1, A-2 and B-1 agents were used as one kit for amplification/detection of the pathogenic Candida yeast (Table 1).

TABLE 1

| | | |
|---|---|---|
| A-1 Agent Candida Primer | A-1 solution 20 μl (1 μl × 20) | |
| A-2 Agent Candida Primer | A-2 solution 20 μl (1 μl × 20) | |

TABLE 1-continued

| | | |
|---|---|---|
| B-1 Agent Candida Probe | B-1 solution 20 μl (1 μl × 20) | |

EFFECTS OF THE INVENTION

As described above in detail, the region of the secretory aspartic proteinase gene of pathogenic Candida yeast is revealed by the present invention. By detecting the region, there are provided a method for detection of a yeast belonging to the genus Candida in a sample solution with high sensitivity and a kit for the detection.

What we claim is:

1. An isolated and purified gene from *Candida albicans* encoding a secretory aspartic acid proteinase and consisting of the DNA sequence described by SEQ ID No. 1.

2. A method for specific detection of *Candida albicans* in a biological sample comprising the following steps:
    (a) isolating a genomic DNA from said sample;
    (b) amplifying said genomic DNA with oligonucleotide primers using a polymerase chain reaction, wherein said primers are selected from the group consisting of the oligonucleotide pair having the sequence shown in the following Formulae 1-3:

5'-GCTGCTGATATTACCGTTG-3' (SEQ ID No. 8)     [1]
and
5'-TGAAGTAGAATCAACATC-3' (SEQ ID No. 12), 5'-GCTGCTGATATTACCGTTG-3' (SEQ ID No. 8)     [2]
and
5'-ACTACCACCGGCTTCATTGG-3' (SEQ ID No. 10), and 5'-GGATCTTCATCTCAAGGTA-3' (SEQ ID No. 9)     [3]
and
5'-TAACCAACCCCTAAAATACC-3' (SEQ ID No. 11);

and (c) detecting if specific amplification of said DNA has occurred as a means of detecting *Candida albicans*.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 1023 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL:

( i v ) ANTI-SENSE:

( v ) FRAGMENT TYPE:

( v i ) ORIGINAL SOURCE:
        ( A ) ORGANISM: Candida albicans
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION: 1-1023
        ( C ) IDENTIFICATION METHOD:
        ( D ) OTHER INFORMATION: /note=
            " E CDS (secretary aspartic proteinase)"

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:1:

-continued

| | | | | | | |
|---|---|---|---|---|---|---|
|CAAGCTGTCC|CAGTGACTTT|ACACAATGAA|CAAGTCACTT|ATGCTGCTGA|TATTACCGTT|60|
|GGATCCAATA|ATCAAAAACT|TAATGTTATT|GTTGATACTG|GATCATCAGA|TTTATGGGTT|120|
|CCTGATGTTA|ATGTTGATTG|TCAAGTCACT|TATAGTGATC|AAACTGCAGA|TTTCTGTAAA|180|
|CAAAAGGGGA|CATATGATCC|AAGTGGTTCA|TCAGCTTCAC|AAGATTTGAA|TACTCCATTC|240|
|AAAATTGGTT|ATGGTGATGG|ATCTTCATCT|CAAGGTACTT|TATATAAGGA|TACCGTTGGA|300|
|TTTGGTGGTG|TTTCGATTAA|AAATCAAGTT|TTAGCTGATG|TTGATTCTAC|TTCAATTGAT|360|
|CAAGGTATTT|TAGGGGTTGG|TTATAAAACC|AATGAAGCCG|GTGGTAGTTA|TGATAATGTC|420|
|CCTGTCACTT|TAAAAAAACA|AGGAGTCATT|GCTAAGAATG|CTTATTCACT|TATCTTAATT|480|
|CTCCAGATGC|TGCCACGGGA|CAAATCATTT|TCGGTGGGGT|TGATAATGCT|AAATATAGTG|540|
|GGTTCATTAA|TTGCATTACC|AGTTACTTCT|GATCGTGAAT|TAAGAATTAG|TTTGGGTTCA|600|
|GTTGAAGTTT|CTGGTAAAAC|CATCAATACT|GATAATGTCG|ATGTTCTTTT|GGATTCAGGT|660|
|ACCACCATTA|CTTATTTGCA|ACAAGATCTT|GCTGATCAAA|TCATTAAAGC|TTTCAATGGT|720|
|AAATTAACTC|AAGATTCCAA|TGGTAATTCA|TTCTATGAAG|TTGATTGTAA|TTTGTCAGGG|780|
|GATGTTGTAT|TCAATTTTAG|TAAAAATGCT|AAAATTTCCG|TTCCAGCTTC|CGAATTTGCT|840|
|GCTTCTTTAC|AAGGTGATGA|TGGTCAACCA|TATGATAAAT|GTCAATTACT|TTTCGATGTT|900|
|AATGATGCTA|ACATTCTTGG|TGATAACTTT|TTGAGATCAC|TTATATTGTT|TATGATTTGG|960|
|ATGATAATGA|AATTTCTTTG|GCTCAAGTCA|AATATACTTC|TCTTCCAGTA|TTTCTCCTTG|1020|
|ACC| | | | | |1023|

( 2 ) INFORMATION FOR SEQ ID NO:2:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( i i i ) HYPOTHETICAL: NO ( i v ) ANTI-SENSE: YES ( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION: 1-37
        ( C ) IDENTIFICATION METHOD:
        ( D ) OTHER INFORMATION: /note="E primer"

( x ) PUBLICATION INFORMATION:
        ( A ) AUTHORS:
        ( B ) TITLE:

( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:2:

```
GTTTTCCCAG TCACGACTTT TTTTTTTTT TTTTTT          37
```

( 2 ) INFORMATION FOR SEQ ID NO:3:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL:

( i v ) ANTI-SENSE:

( v ) FRAGMENT TYPE: N-terminal fragment (secretary aspartic
            proteinase)

( v i ) ORIGINAL SOURCE:
        ( A ) ORGANISM: Candida albicans
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION: 1-1023
        ( C ) IDENTIFICATION METHOD:
        ( D ) OTHER INFORMATION: /note=
            " E CDS (secretary aspartic proteinase)"

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:3:

```
Gln Ala Val Pro Val Thr Leu His Asn Glu Gln Val Thr Tyr Ala
 1               5                   10                  15

Ala Asp Ile Thr Val Gly Ser Asn Xaa Gln Xaa Leu Xaa Asp Ile
                20                  25                  30
```

( 2 ) INFORMATION FOR SEQ ID NO:4:

( i ) SEQUENCE CHARACTERISTICS:
    ( A ) LENGTH: 327 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL:

( i v ) ANTI-SENSE:

( v ) FRAGMENT TYPE:

( v i ) ORIGINAL SOURCE:
    ( A ) ORGANISM: Candida albicans
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:4:

```
GAGCAGGTGA CTTATGCTGC TGATATTACC GTTGGATCCA ATAATCAAAA ACTTAATGTT     60

ATTGTTGATA CTGGATCATC AGATTTATGG GTTCCTGATG TTAATGTTGA TTGTCAAGTC    120

ACTTATAGTG ATCAAACTGC AGATTTCTGT AAACAAAAGG GGACATATGA TCCAAGTGGT    180

TCATCAGCTT CACAAGATTT GAATACTCCA TTCAAAATTG GTTATGGTGA TGGATCTTCA    240

TCTCAAGGTA CTTTATATAA GGATACCGTT GGATTTGGTG GTGTTTCGAT TAAAAATCAA    300

GTTTTAGCTG ATGTTGATTC TACTTCA                                        327
```

( 2 ) INFORMATION FOR SEQ ID NO:5:

( i ) SEQUENCE CHARACTERISTICS:
    ( A ) LENGTH: 933 base pairs
    ( B ) TYPE: nucleic acid
    ( C ) STRANDEDNESS: double
    ( D ) TOPOLOGY: linear ( i i ) MOLECULE TYPE: cDNA to mRNA ( i i i ) HYPOTHETICAL:

( i v ) ANTI-SENSE:

(v) FRAGMENT TYPE:

(vi) ORIGINAL SOURCE:
    (A) ORGANISM: Candida albicans
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:5:

```
GGATCTTCAT CTCAAGGTAC TTTATATAAG GATACCGTTG GATTTGGTGG TGTTTCGATT    60
AAAAATCAAG TTTTAGCTGA TGTTGATTCT ACTTCAATTG ATCAAGGTAT TTAGGGGTT    120
GGTTATAAAA CCAATGAAGC CGGTGGTAGT TATGATAATG TCCCTGTCAC TTTAAAAAAA   180
CAAGGAGTCA TTGCTAAGAA TGCTTATTCA CTTATCTTAA TTCTCCAGAT GCTGCCACGG   240
GACAAATCAT TTTCGGTGGG GTTGATAATG CTAAATATAG TGGGTTCATT AATTGCATTA   300
CCAGTTACTT CTGATCGTGA ATTAAGAATT AGTTGGGTT CAGTTGAAGT TTCTGGTAAA    360
ACCATCAATA CTGATAATGT CGATGTTCTT TTGGATTCAG GTACCACCAT TACTTATTTG   420
CAACAAGATC TTGCTGATCA AATCATTAAA GCTTTCAATG GTAAATTAAC TCAAGATTCC   480
AATGGTAATT CATTCTATGA AGTTGATTGT AATTTGTCAG GGGATGTTGT ATTCAATTTT   540
AGTAAAAATG CTAAAATTTC CGTTCCAGCT TCCGAATTTG CTGCTTCTTT ACAAGGTGAT   600
GATGGTCAAC CATATGATAA ATGTCAATTA CTTTTCGATG TTAATGATGC TAACATTCTT   660
GGTGATAACT TTTTGAGATC ACTTATATTG TTTATGATTT GGATGATAAT GAAATTTCTT   720
TGGCTCAAGT CAAATATACT TCTCTTCCAG TATTTCTCCT TGACCTAAGA TGAAGGGGTG   780
AGATAAAGTT GAAATATTAA AATATTAGTT CTTGATTAGT TTTTACTTAC TTGAAAGGAG   840
TGGCTTTTTT TTTATAGTTT GATAACTTTT TTTGCTTTCT TTCAAGTTTT TTTTATATTT   900
TGTTTTGTTT TGTAAAAAAA AAAAAAAAAA AAA                                933
```

(2) INFORMATION FOR SEQ ID NO:6:

(i) SEQUENCE CHARACTERISTICS:
        (A) LENGTH: 547 base pairs
        (B) TYPE: nucleic acid ( C ) STRANDEDNESS: double
            ( D ) TOPOLOGY: linear ( i i ) MOLECULE TYPE: cDNA to mRNA ( i i i ) HYPOTHETICAL:

( i v ) ANTI-SENSE:

( v ) FRAGMENT TYPE:

( v i ) ORIGINAL SOURCE:
            ( A ) ORGANISM: Candida albicans
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( v i i ) IMMEDIATE SOURCE:
            ( A ) LIBRARY:
            ( B ) CLONE:

( v i i i ) POSITION IN GENOME:
            ( A ) CHROMOSOME/SEGMENT:
            ( B ) MAP POSITION:
            ( C ) UNITS:

( i x ) FEATURE:
            ( A ) NAME/KEY:
            ( B ) LOCATION:
            ( C ) IDENTIFICATION METHOD:
            ( D ) OTHER INFORMATION:

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:

( x i ) SEQUENCE DESCRIPTION: SEQ ID NO:6:

| | | | | | |
|---|---|---|---|---|---|
| TTTTTAAAGA | ATATTTTCAT | GGCCTTGCTA | TTGCTTTATT | AGTCGATGCT | ACTCCAACAA | 60 |
| CAACCAAAAG | ATCAGCTGGT | TTCGTTGCTT | TAGATTTCAG | TGTTGTGAAA | ACTCCTAAAG | 120 |
| CATCCCCAGT | TACTAATGGC | CAAGAAGGTA | AAACTTCCAA | AAGACAAGCT | GTCCCAGTGA | 180 |
| CTTTACACAA | TGAACAAGTC | ACTTATGCTG | CTGATATTAC | CGTTGGATCC | AATAATCAAA | 240 |
| AACTTAATGT | TATTGTTGAT | ACTGGATCAT | CAGATTTATG | GGTTCCTGAT | GTTAATGTTG | 300 |
| ATTGTCAAGT | CACTTATAGT | GATCAAACTG | CAGATTTCTG | TAAACAAAAG | GGGACATATG | 360 |
| ATCCAAGTGG | TTCATCAGCT | TCACAAGATT | TGAATACTCC | ATTCAAAATT | GGTTATGGTG | 420 |
| ATGGATCTTC | ATCTCAAGGT | ACTTTATATA | AGGATACCGT | TGGATTTGGT | GGTGTTTCGA | 480 |
| TTAAAAATCA | AGTTTTAGCT | GATGTTGATT | CTACTTCAAT | TGATCAAGGT | ATTTTAGGGG | 540 |
| TTGGTTA | | | | | | 547 |

( 2 ) INFORMATION FOR SEQ ID NO:7:

( i ) SEQUENCE CHARACTERISTICS:
            ( A ) LENGTH: 1355 base pairs
            ( B ) TYPE: nucleic acid
            ( C ) STRANDEDNESS: double
            ( D ) TOPOLOGY: linear ( i i ) MOLECULE TYPE: cDNA to mRNA (iii) HYPOTHETICAL:

(iv) ANTI-SENSE:

(v) FRAGMENT TYPE:

(vi) ORIGINAL SOURCE:
    (A) ORGANISM: Candida albicans
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION: 165-1187
    (C) IDENTIFICATION METHOD:
    (D) OTHER INFORMATION: /note=
        " E CDS (secretary aspartic proteinase)"

(ix) FEATURE:
    (A) NAME/KEY:
    (B) LOCATION: 1336-1355
    (C) IDENTIFICATION METHOD:
    (D) OTHER INFORMATION: /note="E poly A site"

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:7:

```
TTTTTAAAGA ATATTTTCAT GGCCTTGCTA TTGCTTTATT AGTCGATGCT ACTCCAACAA        60

CAACCAAAAG ATCAGCTGGT TTCGTTGCTT TAGATTTCAG TGTTGTGAAA ACTCCTAAAG       120

CATCCCCAGT TACTAATGGC CAAGAAGGTA AAACTTCCAA AAGA CAA GCT GTC CCA       176
                                                 Gln Ala Val Pro
                                                  1

GTG ACT TTA CAC AAT GAA CAA GTC ACT TAT GCT GCT GAT ATT ACC            221
Val Thr Leu His Asn Glu Gln Val Thr Tyr Ala Ala Asp Ile Thr
 5            10                  15

GTT GGA TCC AAT AAT CAA AAA CTT AAT GTT ATT GTT GAT ACT GGA            266
Val Gly Ser Asn Asn Gln Lys Leu Asn Val Ile Val Asp Thr Gly
 20               25                   30

TCA TCA GAT TTA TGG GTT CCT GAT GTT AAT GTT GAT TGT CAA GTC            311
Ser Ser Asp Leu Trp Val Pro Asp Val Asn Val Asp Cys Gln Val
 35               40                  45

ACT TAT AGT GAT CAA ACT GCA GAT TTC TGT AAA CAA AAG GGG ACA            356
Thr Tyr Ser Asp Gln Thr Ala Asp Phe Cys Lys Gln Lys Gly Thr
 50               55                  60

TAT GAT CCA AGT GGT TCA TCA GCT TCA CAA GAT TTG AAT ACT CCA            401
Tyr Asp Pro Ser Gly Ser Ser Ala Ser Gln Asp Leu Asn Thr Pro
```

```
               65                      70                        75

TTC  AAA  ATT  GGT  TAT  GGT  GAT  GGA  TCT  TCA  TCT  CAA  GGT  ACT  TTA      446
Phe  Lys  Ile  Gly  Tyr  Gly  Asp  Gly  Ser  Ser  Ser  Gln  Gly  Thr  Leu
 80                      85                        90

TAT  AAG  GAT  ACC  GTT  GGA  TTT  GGT  GGT  GTT  TCG  ATT  AAA  AAT  CAA      491
Tyr  Lys  Asp  Thr  Val  Gly  Phe  Gly  Gly  Val  Ser  Ile  Lys  Asn  Gln
 95                     100                       105

GTT  TTA  GCT  GAT  GTT  GAT  TCT  ACT  TCA  ATT  GAT  CAA  GGT  ATT  TTA      536
Val  Leu  Ala  Asp  Val  Asp  Ser  Thr  Ser  Ile  Asp  Gln  Gly  Ile  Leu
110                      115                       120

GGG  GTT  GGT  TAT  AAA  ACC  AAT  GAA  GCC  GGT  GGT  AGT  TAT  GAT  AAT      581
Gly  Val  Gly  Tyr  Lys  Thr  Asn  Glu  Ala  Gly  Gly  Ser  Tyr  Asp  Asn
125                      130                       135

GTC  CCT  GTC  ACT  TTA  AAA  AAA  CAA  GGA  GTC  ATT  GCT  AAG  AAT  GCT      626
Val  Pro  Val  Thr  Leu  Lys  Lys  Gln  Gly  Val  Ile  Ala  Lys  Asn  Ala
140                      145                       150

TAT  TCA  CTT  ATC  TTA  ATT  CTC  CAG  ATG  CTG  CCA  CGG  GAC  AAA  TCA      671
Tyr  Ser  Leu  Ile  Leu  Ile  Leu  Gln  Met  Leu  Pro  Arg  Asp  Lys  Ser
155                      160                       165

TTT  TCG  GTG  GGG  TTG  ATA  ATG  CTA  AAT  ATA  GTG  GGT  TCA  TTA  ATT      716
Phe  Ser  Val  Gly  Leu  Ile  Met  Leu  Asn  Ile  Val  Gly  Ser  Leu  Ile
170                      175                       180

GCA  TTA  CCA  GTT  ACT  TCT  GAT  CGT  GAA  TTA  AGA  ATT  AGT  TTG  GGT      761
Ala  Leu  Pro  Val  Thr  Ser  Asp  Arg  Glu  Leu  Arg  Ile  Ser  Leu  Gly
185                      190                       195

TCA  GTT  GAA  GTT  TCT  GGT  AAA  ACC  ATC  AAT  ACT  GAT  AAT  GTC  GAT      806
Ser  Val  Glu  Val  Ser  Gly  Lys  Thr  Ile  Asn  Thr  Asp  Asn  Val  Asp
200                      205                       210

GTT  CTT  TTG  GAT  TCA  GGT  ACC  ACC  ATT  ACT  TAT  TTG  CAA  CAA  GAT      851
Val  Leu  Leu  Asp  Ser  Gly  Thr  Thr  Ile  Thr  Tyr  Leu  Gln  Gln  Asp
215                      220                       225

CTT  GCT  GAT  CAA  ATC  ATT  AAA  GCT  TTC  AAT  GGT  AAA  TTA  ACT  CAA      896
Leu  Ala  Asp  Gln  Ile  Ile  Lys  Ala  Phe  Asn  Gly  Lys  Leu  Thr  Gln
230                      235                       240

GAT  TCC  AAT  GGT  AAT  TCA  TTC  TAT  GAA  GTT  GAT  TGT  AAT  TTG  TCA      941
Asp  Ser  Asn  Gly  Asn  Ser  Phe  Tyr  Glu  Val  Asp  Cys  Asn  Leu  Ser
245                      250                       255

GGG  GAT  GTT  GTA  TTC  AAT  TTT  AGT  AAA  AAT  GCT  AAA  ATT  TCC  GTT      986
Gly  Asp  Val  Val  Phe  Asn  Phe  Ser  Lys  Asn  Ala  Lys  Ile  Ser  Val
260                      265                       270

CCA  GCT  TCC  GAA  TTT  GCT  GCT  TCT  TTA  CAA  GGT  GAT  GAT  GGT  CAA     1031
Pro  Ala  Ser  Glu  Phe  Ala  Ala  Ser  Leu  Gln  Gly  Asp  Asp  Gly  Gln
275                      280                       285

CCA  TAT  GAT  AAA  TGT  CAA  TTA  CTT  TTC  GAT  GTT  AAT  GAT  GCT  AAC     1076
Pro  Tyr  Asp  Lys  Cys  Gln  Leu  Leu  Phe  Asp  Val  Asn  Asp  Ala  Asn
290                      295                       300

ATT  CTT  GGT  GAT  AAC  TTT  TTG  AGA  TCA  CTT  ATA  TTG  TTT  ATG  ATT     1121
Ile  Leu  Gly  Asp  Asn  Phe  Leu  Arg  Ser  Leu  Ile  Leu  Phe  Met  Ile
305                      310                       315

TGG  ATG  ATA  ATG  AAA  TTT  CTT  TGG  CTC  AAG  TCA  AAT  ATA  CTT  CTC     1166
Trp  Met  Ile  Met  Lys  Phe  Leu  Trp  Leu  Lys  Ser  Asn  Ile  Leu  Leu
320                      325                       330

TTC  CAG  TAT  TTC  TCC  TTG  ACC  TAAGATGAAG  GGGTGAGATA  AAGTTGAAAT         1217
Phe  Gln  Tyr  Phe  Ser  Leu  Thr
335                      340

ATTAAAATAT  TAGTTCTTGA  TTAGTTTTTA  CTTACTTGAA  AGGAGTGGCT  TTTTTTTTAT      1277

AGTTTGATAA  CTTTTTTTGC  TTTCTTTCAA  GTTTTTTTTA  TATTTGTTT   TGTTTTGTAA      1337

AAAAAAAAAA  AAAAAAA                                                         1355

( 2 ) INFORMATION FOR SEQ ID NO:8:
```

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid (synthetic DNA)

( i i i ) HYPOTHETICAL: NO ( i v ) ANTI-SENSE: NO ( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION: 1-19
    ( C ) IDENTIFICATION METHOD:
    ( D ) OTHER INFORMATION: /note="E primer"

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:8:

GCTGCTGATA TTACCGTTG    19

( 2 ) INFORMATION FOR SEQ ID NO:9:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid (synthetic DNA)

( i i i ) HYPOTHETICAL: NO ( i v ) ANTI-SENSE: NO ( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:

(G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION: 1-19
                (C) IDENTIFICATION METHOD:
                (D) OTHER INFORMATION: /note="E primer"

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:9:

GGATCTTCAT CTCAAGGTA        19

(2) INFORMATION FOR SEQ ID NO:10:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: other nucleic acid (synthetic DNA)

(iii) HYPOTHETICAL: NO (iv) ANTI-SENSE: YES (v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION: 1-20
                (C) IDENTIFICATION METHOD:
                (D) OTHER INFORMATION: /note="E primer"

(x) PUBLICATION INFORMATION:
                (A) AUTHORS:
                (B) TITLE:

(C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(x i) SEQUENCE DESCRIPTION: SEQ ID NO:10:

ACTACCACCG GCTTCATTGG        20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (synthetic DNA)

(iii) HYPOTHETICAL: NO (iv) ANTI-SENSE: YES (v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION: 1-20
        (C) IDENTIFICATION METHOD:
        (D) OTHER INFORMATION: /note="E primer"

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(x i) SEQUENCE DESCRIPTION: SEQ ID NO:11:

TAACCAACCC CTAAAATACC        20

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear ( i i ) MOLECULE TYPE: other nucleic acid (synthetic DNA)

( i i i ) HYPOTHETICAL: NO ( i v ) ANTI-SENSE: YES ( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION: 1-18
    ( C ) IDENTIFICATION METHOD:
    ( D ) OTHER INFORMATION: /note="E primer"

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:12:

TGAAGTAGAA TCAACATC    18

( 2 ) INFORMATION FOR SEQ ID NO:13:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid (synthetic DNA)

( i i i ) HYPOTHETICAL: NO ( i v ) ANTI-SENSE: NO ( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:

( B ) CLONE:

( v i i i ) POSITION IN GENOME:
               ( A ) CHROMOSOME/SEGMENT:
               ( B ) MAP POSITION:
               ( C ) UNITS:

( i x ) FEATURE:
               ( A ) NAME/KEY:
               ( B ) LOCATION: 1-20
               ( C ) IDENTIFICATION METHOD:
               ( D ) OTHER INFORMATION: /note="E probe"

( x ) PUBLICATION INFORMATION:
               ( A ) AUTHORS:
               ( B ) TITLE:
               ( C ) JOURNAL:
               ( D ) VOLUME:
               ( E ) ISSUE:
               ( F ) PAGES:
               ( G ) DATE:
               ( H ) DOCUMENT NUMBER:
               ( I ) FILING DATE:
               ( J ) PUBLICATION DATE:
               ( K ) RELEVANT RESIDUES IN SEQ ID NO:

( x i ) SEQUENCE DESCRIPTION: SEQ ID NO:13:

TTGGATTTGG TGGTGTTTCG          20

( 2 ) INFORMATION FOR SEQ ID NO:14:

( i ) SEQUENCE CHARACTERISTICS:
               ( A ) LENGTH: 17 base pairs
               ( B ) TYPE: nucleic acid
               ( C ) STRANDEDNESS: single
               ( D ) TOPOLOGY: linear ( i i ) MOLECULE TYPE: other nucleic acid (synthetic DNA)

( i i i ) HYPOTHETICAL: NO ( i v ) ANTI-SENSE: NO ( v ) FRAGMENT TYPE:

( v i ) ORIGINAL SOURCE:
               ( A ) ORGANISM:
               ( B ) STRAIN:
               ( C ) INDIVIDUAL ISOLATE:
               ( D ) DEVELOPMENTAL STAGE:
               ( E ) HAPLOTYPE:
               ( F ) TISSUE TYPE:
               ( G ) CELL TYPE:
               ( H ) CELL LINE:
               ( I ) ORGANELLE:

( v i i ) IMMEDIATE SOURCE:
               ( A ) LIBRARY:
               ( B ) CLONE:

( v i i i ) POSITION IN GENOME:
               ( A ) CHROMOSOME/SEGMENT:
               ( B ) MAP POSITION:
               ( C ) UNITS:

( i x ) FEATURE:
               ( A ) NAME/KEY:
               ( B ) LOCATION: 1-17
               ( C ) IDENTIFICATION METHOD:
               ( D ) OTHER INFORMATION: /note="E primer"

( x ) PUBLICATION INFORMATION:
               ( A ) AUTHORS:
               ( B ) TITLE:
               ( C ) JOURNAL:
               ( D ) VOLUME:
               ( E ) ISSUE:
               ( F ) PAGES:
               ( G ) DATE:
               ( H ) DOCUMENT NUMBER:

( I ) FILING DATE:
( J ) PUBLICATION DATE:
( K ) RELEVANT RESIDUES IN SEQ ID NO:

( x i ) SEQUENCE DESCRIPTION: SEQ ID NO:14:

CARGCNGTNC CNGTNAC 17

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( i i i ) HYPOTHETICAL: NO ( i v ) ANTI-SENSE: NO ( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION: 1-20
        ( C ) IDENTIFICATION METHOD:
        ( D ) OTHER INFORMATION: /note="E primer"

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:15:

CAYAAYGARC ARGTNACNTA 20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( i i i ) HYPOTHETICAL: NO ( i v ) ANTI-SENSE: NO (v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION: 1-20
    (C) IDENTIFICATION METHOD:
    (D) OTHER INFORMATION: /note="E probe"

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:16:

GCNGCNGAYA THACNGTNGG    20